United States Patent [19]

Masukawa et al.

[11] Patent Number: 4,788,284
[45] Date of Patent: Nov. 29, 1988

[54] DIPHENYLIMIDAZOLE TYPE DYES

[75] Inventors: Toyoaki Masukawa; Yasuo Tsuda; Hidetaka Ninomiya; Noritaka Nakayama, all of Hino, Japan

[73] Assignee: Konishiroku Photo Industry Co., Ltd., Tokyo, Japan

[21] Appl. No.: 84,311

[22] Filed: Aug. 10, 1987

Related U.S. Application Data

[63] Continuation-in-part of Ser. No. 60,057, Jun. 9, 1987.

[30] Foreign Application Priority Data

Jun. 13, 1986 [JP] Japan ................................. 61-138868

[51] Int. Cl.$^4$ ................. C07D 403/12; C07D 401/12; C07D 233/96
[52] U.S. Cl. ..................................... 544/139; 544/370; 546/210; 548/301; 548/315; 548/316
[58] Field of Search ........................ 548/301, 315, 316; 544/139, 370; 546/210

[56] References Cited

U.S. PATENT DOCUMENTS 4,492,709  1/1985  Purcell ............................ 548/315 X Primary Examiner—Richard A. Schwartz
Attorney, Agent, or Firm—Jordan B. Bierman

[57] ABSTRACT

A diphenylimidazole type cyan dye represented by the following Formula [I] or [II] is disclosed. The dye is capable of displaying relatively more preferable absorption characteristics so as to serve as a cyan dye, and suitable to be use in photographic, thermal transfer, ink-jet, printing or other printing media.

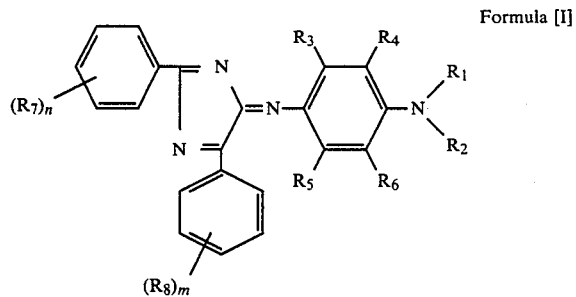

Formula [I]

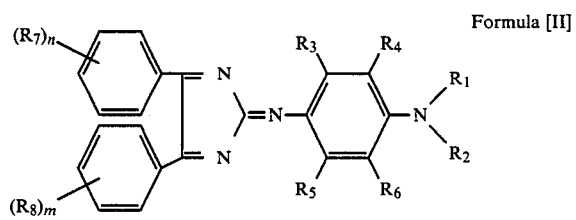

Formula [II]

7 Claims, No Drawings

DIPHENYLIMIDAZOLE TYPE DYES

This application is a continuation-in-part of copending application Ser. No. 060,057 filed June 9, 1987.

FIELD OF THE INVENTION

This invention relates to a novel diphenylimidazole type dye useful for forming a color image, a filter and so forth.

BACKGROUND OF THE INVENTION

British Pat. No. 1,545,507 discloses that a diphenylimidazole forms a dye upon the oxidation coupling thereof to an aminophenol and that such a diphenylimidazole is useful for forming a coupler for photographic use and such a dye which is formed upon the oxidation coupling of diphenylimidazoles to aminophenols is capable of reproduce an image excellent in light-fastness through a mordant treatment applied thereto with a quaternary ammonium mordant.

However, in the dyes formed through such an oxidation coupling of a diphenylimidazole to an aminophenol, an image color reproduction depends upon pH values. If a pH is neutral, a λ maximum of absorption wavelength is substantially inclined to a short wavelength region. Therefore, it is essential to make a quaternary mordant present whenever such a dye is used so as to reproduce an image.

In such a system not having any of such a mordant present, a λ max of light absorption of these dyes will shift into the green spectral region of the visible light region. Therefore, these dyes cannot be applied as cyan dyes to a variety of image-forming means in color reproduction processes and, more particularly, in color subtraction process which is to be applied to photographic, thermal-transfer, ink-jet, printing and other image forming techniques.

As the result of devoting the inventors themselves in various studies, they have finally achieved this invention upon having found the fact that it is possible to obtain a compound which is suitable to serve as a cyan dye and is less in pH dependence, not necessary for any mordant, capable of displaying more preferably spectral absorption characteristics for a cyan dye and excellent in light-fastness, when a specific paraphenylenediamine compound is used in place of the aforementioned aminophenols.

SUMMARY OF THE INVENTION

It is a principal object of the invention to provide a cyan dye relatively less in pH dependence, not necessary for any mordant to be used, capable of displaying relatively more preferable absorption characteristics so as to serve as a cyan dye, and suitable to be used in photographic, thermal-transfer, ink-jet, printing or other image-forming media.

The above-mentioned object of the invention can be achieved with the dyes described below:

Namely, the diphenylimidazole type dyes characterized in having the following formula [I] or [II]:

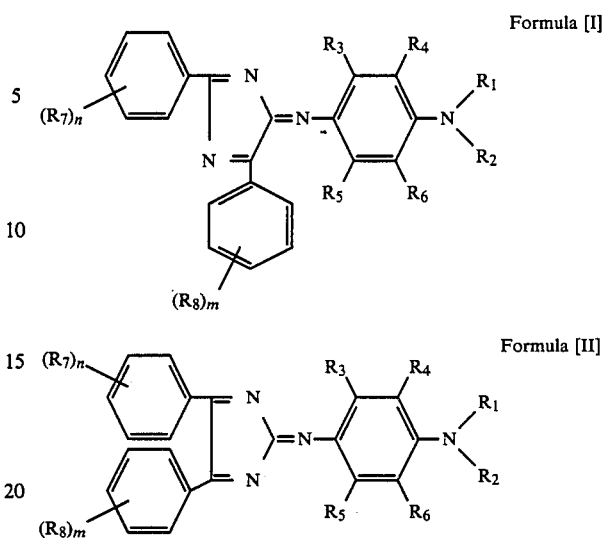

Wherein $R_1$ and $R_2$ represent each a hydrogen atom, an alkyl group or a substituted alkyl group, and $R_1$ and $R_2$ may be coupled to each other so as to complete a 5- or 6-membered ring; $R_3$, $R_4$, $R_5$ and $R_6$ represent each a halogen atom, an alkyl group, a substituted alkyl group, an alkoxy group or a substituted alkoxy group; $R_7$ and $R_8$ represent each a halogen atom or a monovalent substituent; n and m are each an integer of from 0 to 5, provided that, if n is an integer of not less than 2, $R_7$s may be the same with or the different from each other and that, if m is an integer of not less than 2, $R_8$s may be the same with or the different from each other.

In Formulas [I] and [II], $R_1$ and $R_2$ include, preferably, a hydrogen atom, an alkyl group and such a substituted alkyl group as a hydroxyalkyl group, an alkoxyalkyl group, an alkoxyalkoxyalkyl group, an alkylsulfonamidoalkyl group and so forth. The examples of these groups include an alkyl group having 1 to 18 carbon atoms, such as a methyl group, an ethyl group, a propyl group, an isopropyl group, a sec-butyl group, a butyl group, an isobutyl group, a tert-butyl group, an octyl group, a dodecyl group, an octadecyl group, a cyclohexyl group and so forth; a hydroxyethyl group, a methoxyethyl group, a methoxybutyl group, an ethoxyethyl group, a methoxyethoxyethyl group, an ethoxyethoxyethyl group, a β-methanesulfonamidethyl group; and so forth.

The 5- or 6-membered rings each formed by coupling $R_1$ to $R_2$ include, for example, a pyrrolidino group, a piperidino group, a piperazino group, a morpholino group and so forth.

$R_3$, $R_4$, $R_5$ and $R_6$ may be the same with or the different from each other, and they include, for example, a hydrogen atom, a halogen atom, an alkyl group, a hydroxyalkyl group, an alkoxyalkyl group, an alkylsulfonamidalkyl group, an alkoxy group and so forth. The typical examples thereof include a chlorine atom, a bromine atom, a methyl group, an ethyl group, a hydroxymethyl group, a hydroxyethyl group, a methoxyethyl group, a methanesulfonamidethyl group, a methoxy group, an ethoxy group and so forth.

The halogen atoms represented by $R_7$ and $R_8$ are preferably a chlorine atom and a bromine atom. The monovalent organic groups include, for example, those denoted by $R_3$ through $R_6$, a nitro group a hydroxy group an amino group, an alkylamido group which may be substituted, an arylamido group which may be substituted (including, preferably, a substituted or unsubstituted benzamido group), an alkylsulfonamido group which may be substituted, an arylsulfonamido group which may be substituted, a dialkylcarbamoylamino group, a dialkylsulfamoylamino group, an alkoxycarbonylamino group, an aryloxycarbonylamino group, an arylcarbamoylamino group and so forth.

In particular, it is preferable, from the viewpoint of the absorption wavelength of a cyan dye, that the diphenylimidazole type dyes have the group having a hydrogen atom capable of forming a hydrogen-bond with one of the nitrogen atoms of the imidazole ring in each ortho position of the phenyl group thereof to the position of coupling the phenyl group to the imidazole ring thereof, provided that the phenyl group is coupled to the 2nd and 4th positions of the imidazole ring in Formula [I] and to the 4th and 5th positions of the imidazole ring in Formula [II].

The above groups each having a hydrogen atom capable of forming a hydrogen-bond include, for example, a hydroxy group, an amino group, an alkylamido group which may be substituted, an arylamido group which may be substituted (such as, preferably, a substituted or unsubstituted benzamido group) an alkylsulfonamido group which may be substituted, an arylsulfonamido group which may be substituted, a dialkylcarbamoylamino group, a dialkylsulfamoylamino group, an alkoxycarbonylamino group, an aryloxycarbonylamino group, an arylcarbamoylamino group and so forth.

The typical examples of the monovalent organic groups each represented by $R_7$ and $R_8$ include an alkyl group having 1 to 18 carbon atoms such as those of a methyl group, an ethyl group, a sec-butyl group, a tert-octyl group, a dodecyl group and so forth; an alkoxy group having 1 to 18 carbon atoms such as those of a methoxy group, an isopropoxy group, a dodecyloxy group, an octadecyloxy group and so forth; an alkylamido group having 1 to 22 carbon atoms such as an acetamido group, a laurylamido group and so forth; a phenoxyalkylamido group such as a 2,4-di-tert-amylphenoxyacetamido group a m-pentadecylphenoxybutylamido group and so forth; a halogen-substituted alkylamido group such as a chloracetamido group, a trifluoracetamido group, a parfluorobutanamido group and so forth; a substituted benzamido group such as a benzamido group, a naphthoic acid amido group, an o-dodecyloxybenzamido group, a m-laurylamidobenzamido group, a p-tert-butylbenzamido group, a m-α-(2,4-di-tert-amylphenoxy)butanamidobenzamido group and so forth; an alkanesulfonamido group having 1 to 18 carbon atoms such as a methanesulfamido group, a dodecanesulfonamido group and so forth; a non-substituted arylsulfonamido group such as a benzenesulfonamido group and so forth; a p-toluenesulfonamido group; a dodecylbenzenesulfonamido group; a p-dodecyloxybenzenesulfonamido group; and so forth.

The non-substituted alkoxycarbonylamino groups are straight-chained or branched alkoxycarbonylamino groups each having 1 to 22 carbon atoms. Those groups include, for example, n-butoxycarbonylamino groups and 2-ethylhexyloxycarbonylamino groups. The typical examples of the aryloxycarbonylamino groups include a phenoxycarbonylamino group. The typical examples of the arylcarbamoylamino groups include non-substituted arylcarbamoylamino groups such as a phenylcarbamoylamino group, substituted ohenylcarbamoylamino groups each substituted with such a monovalent group as halogen atoms such as a chlorine atom, a cyano group and so forth.

Typical exemplified compounds of the diphenylimidazole type dyes of the invention will now be given below:

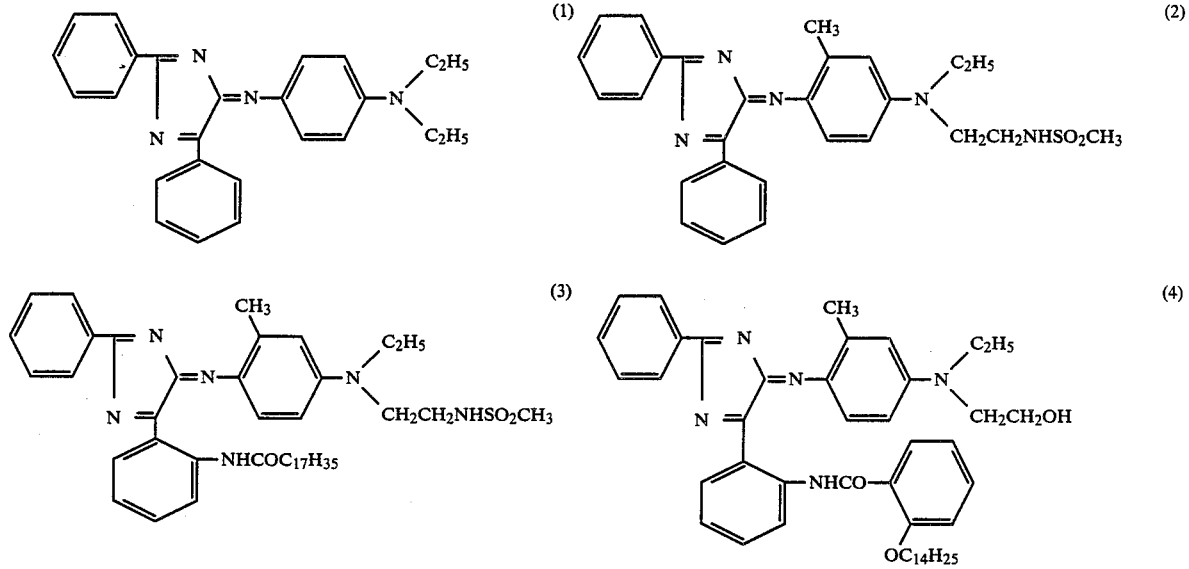

-continued
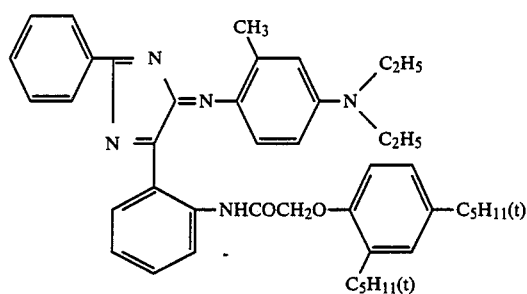 (5)
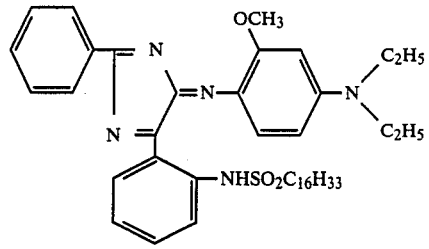 (6)
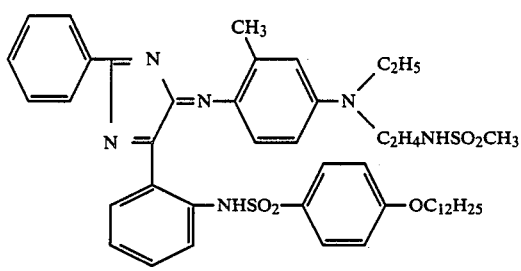 (7)
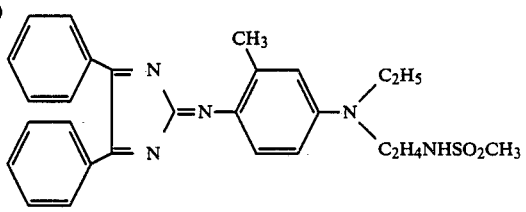 (8)
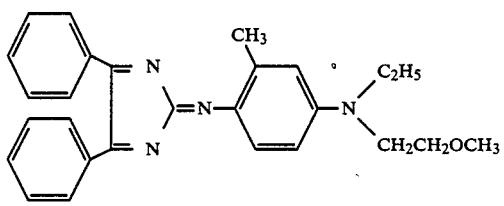 (9)
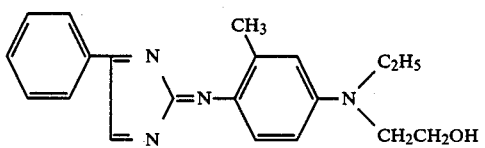 (10)
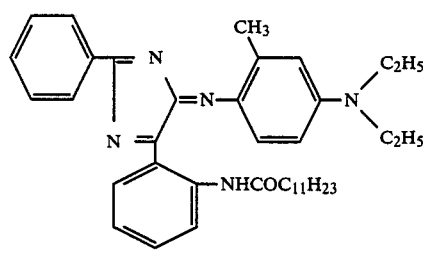 (11)
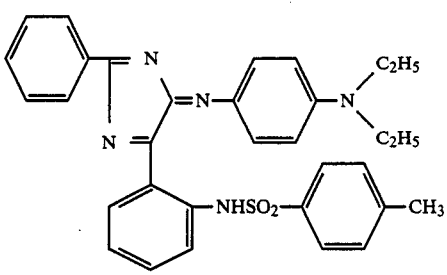 (12)
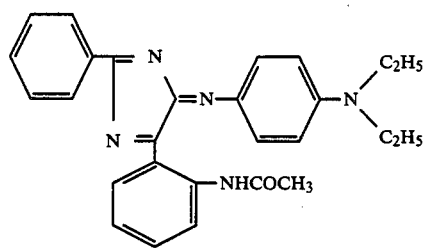 (13)
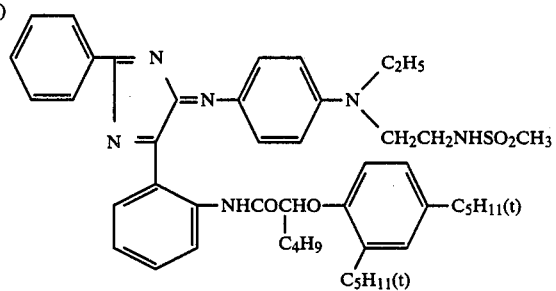 (14)
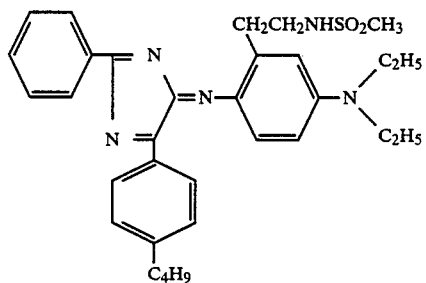 (15)
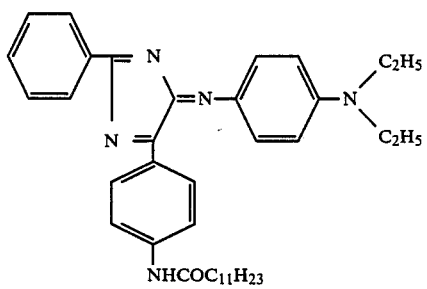 (16)

-continued
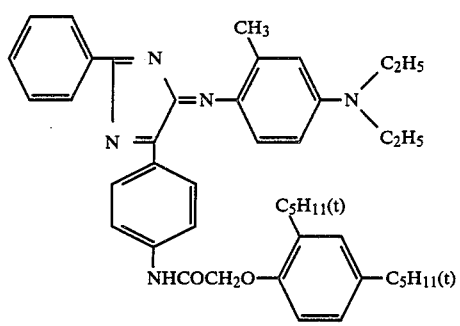 (17)
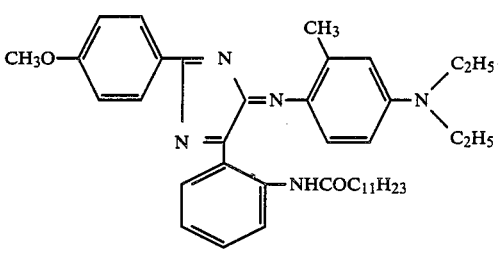 (18)
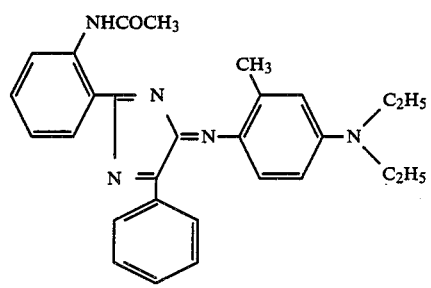 (19)
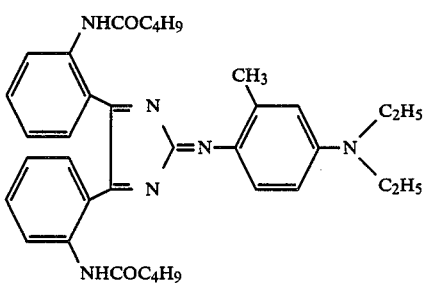 (20)
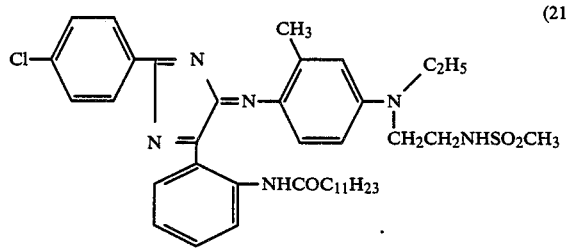 (21)
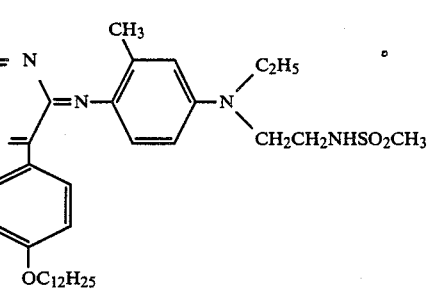 (22)
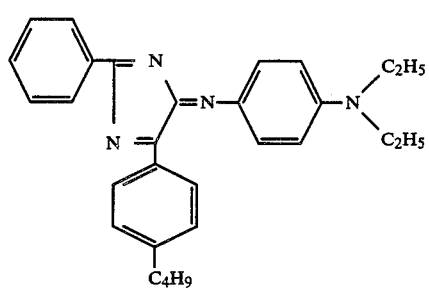 (23)
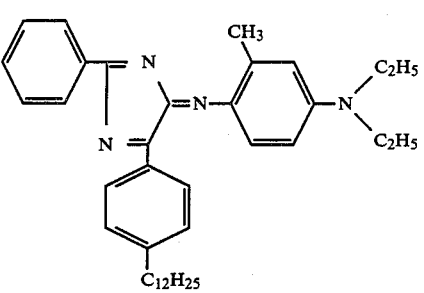 (24)
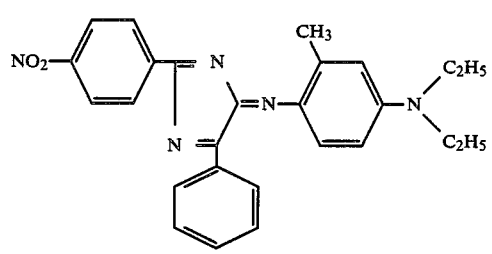 (25)
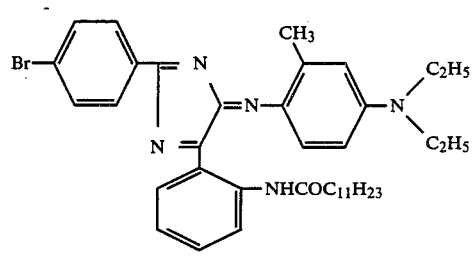 (26)

-continued
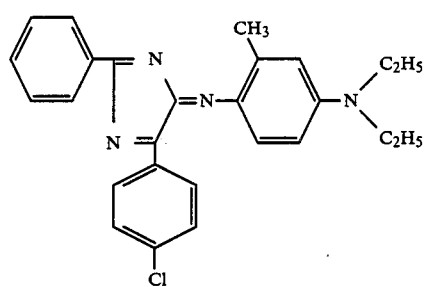 (27)
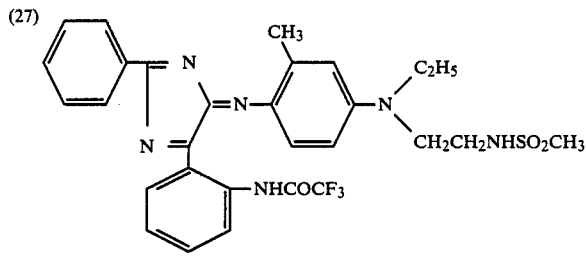 (28)
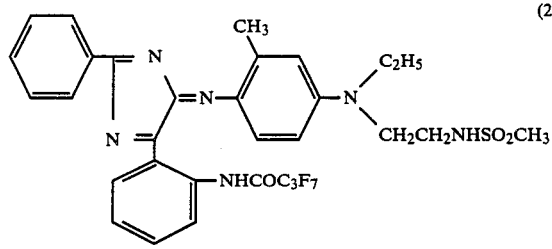 (29)
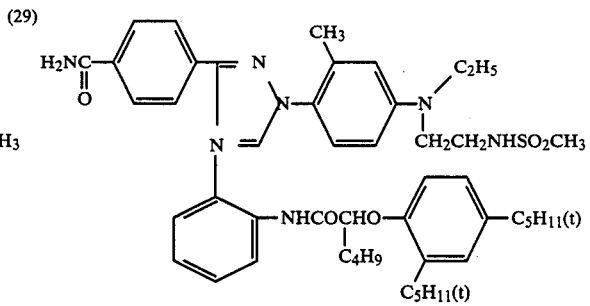 (30)
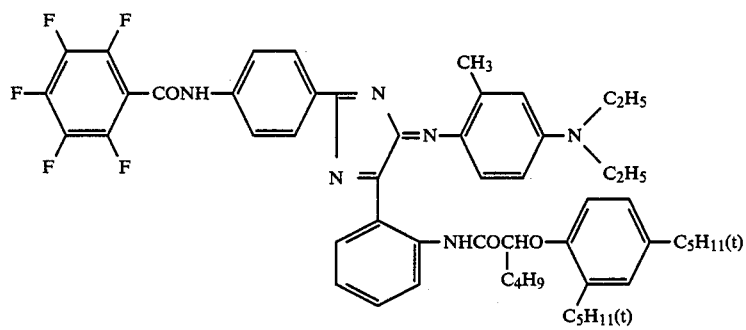 (31)
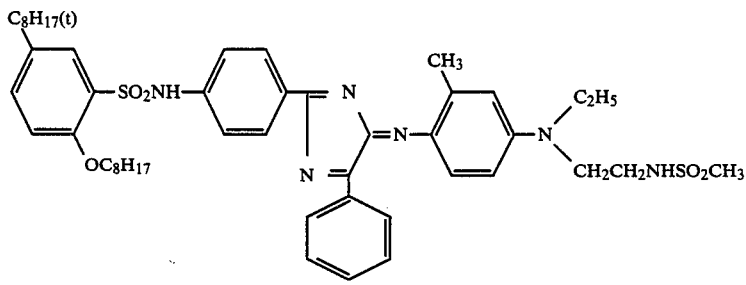 (32)
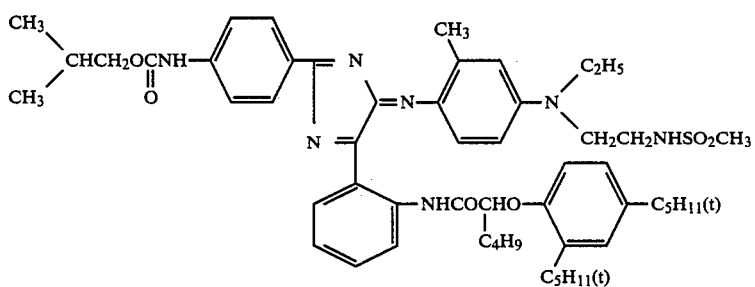 (33)

-continued
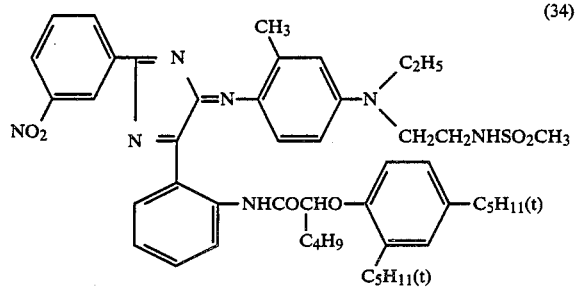 (34)
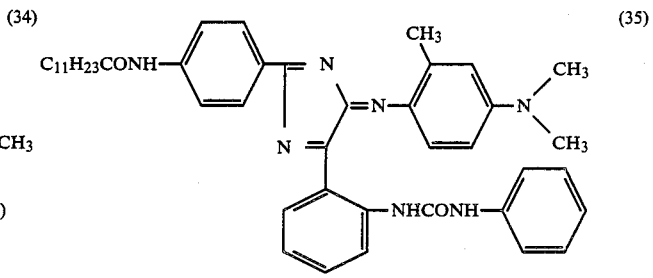 (35)
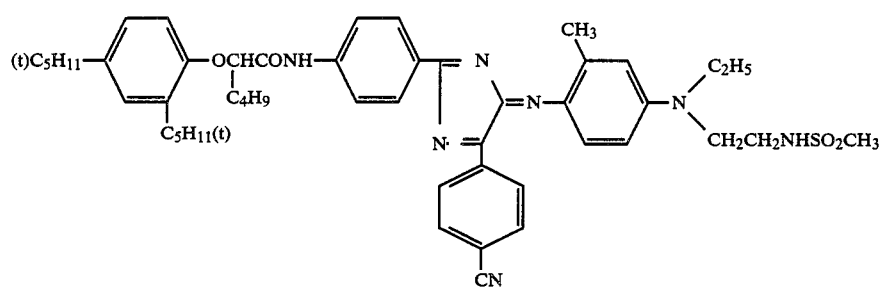 (36)
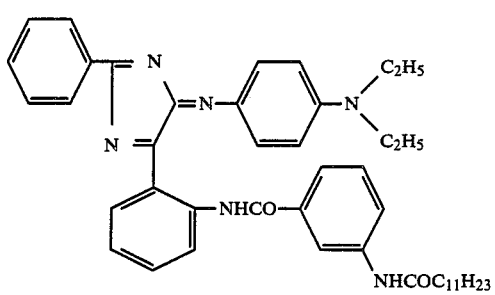 (37)
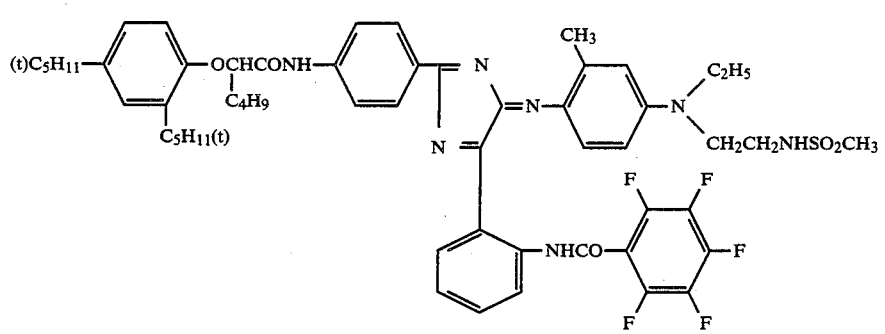 (38)
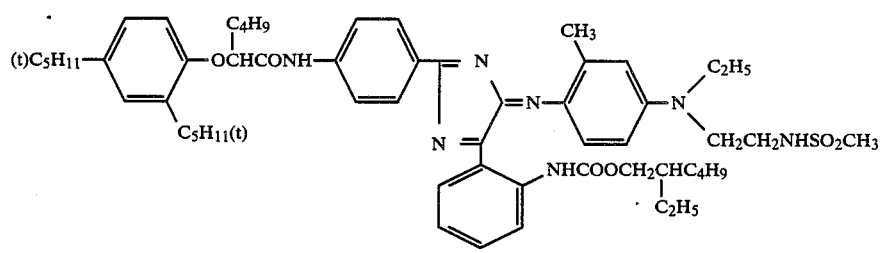 (39)

-continued
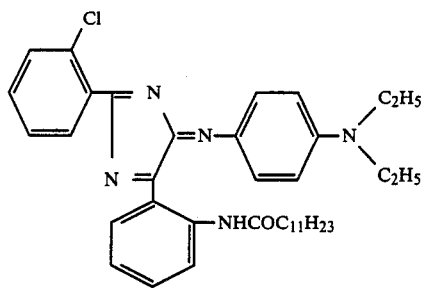
(40)
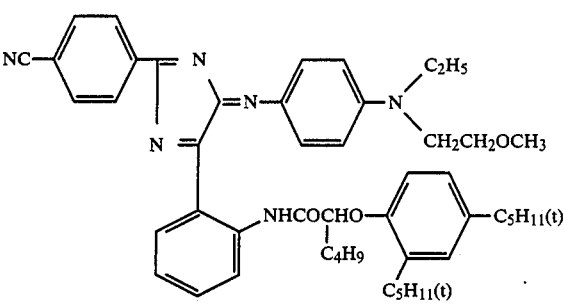
(41)
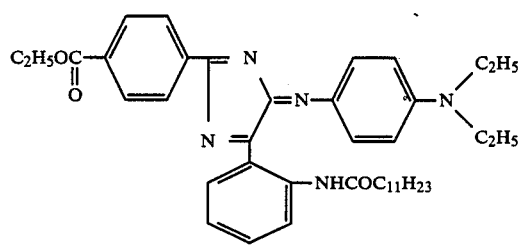
(42)
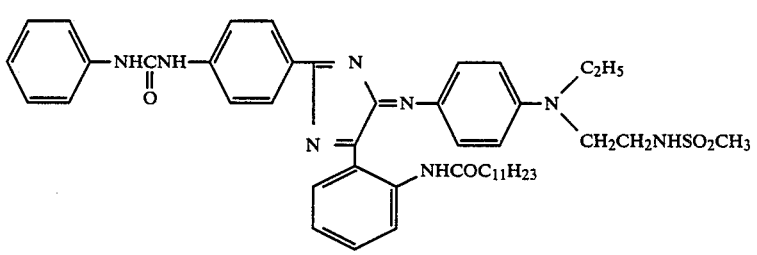
(43)
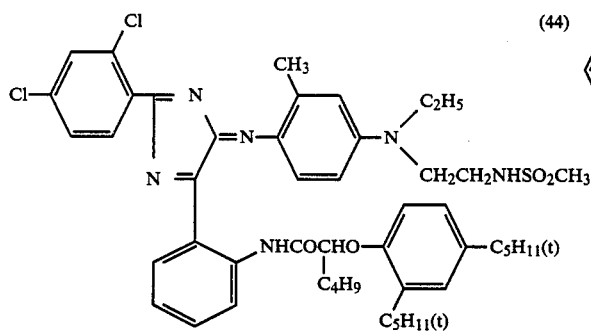
(44)
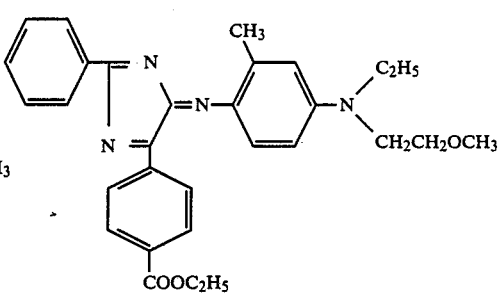
(45)
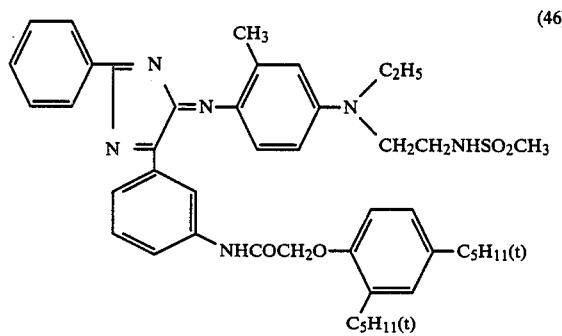
(46)
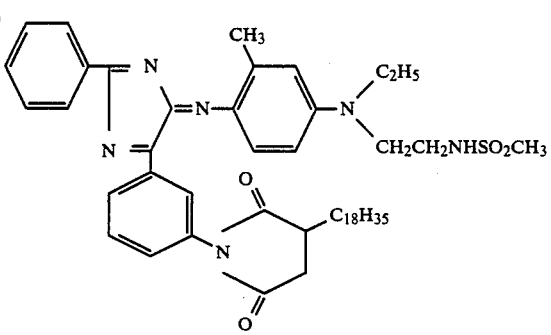
(47)

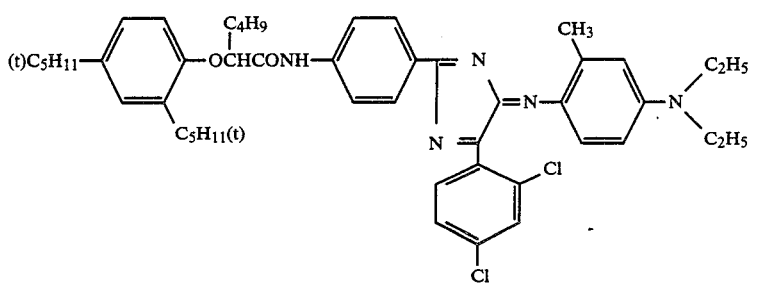
(48)
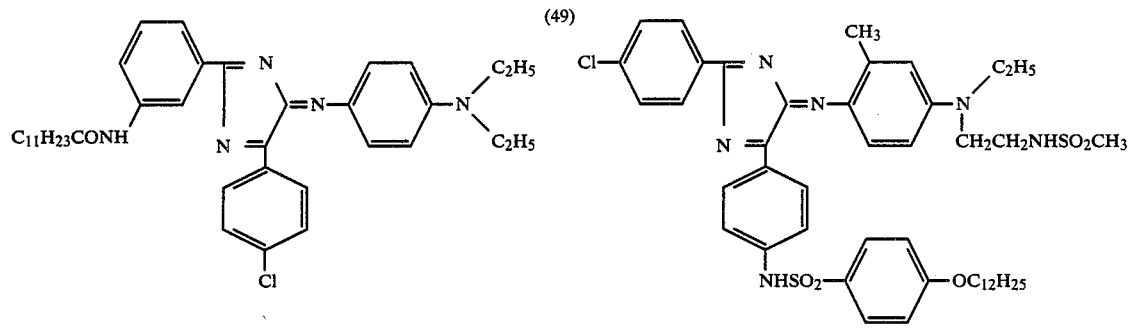
(49) (50)
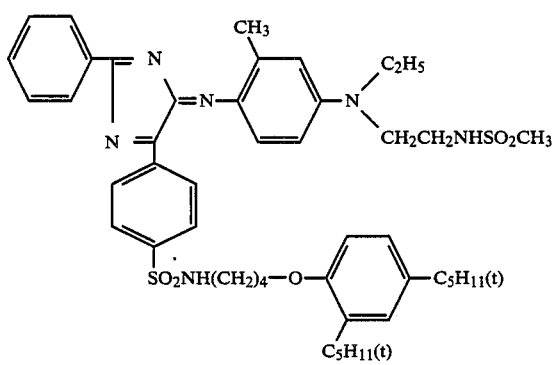
(51)
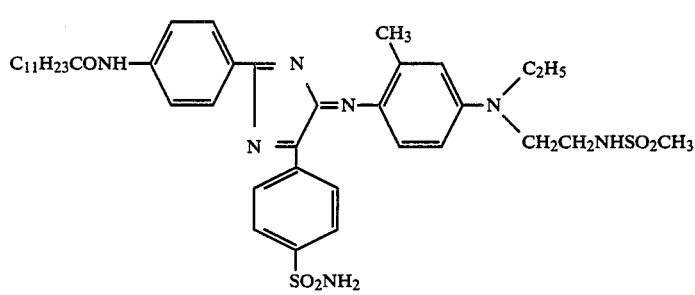
(52)
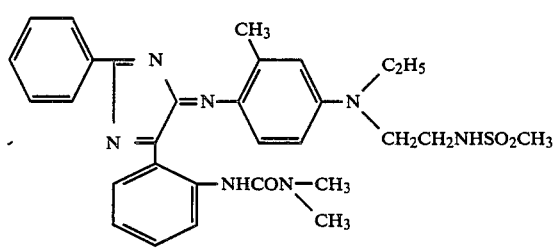
(53)

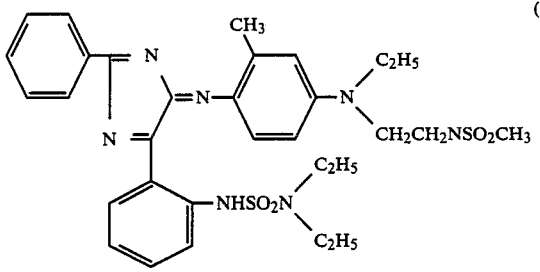 (54)

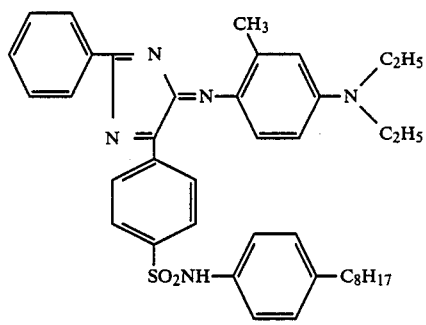 (55)

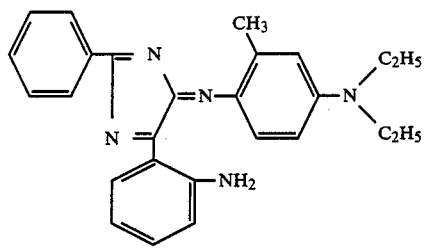 (56)

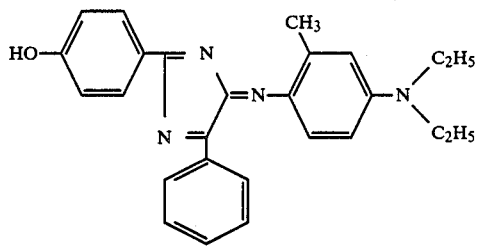 (57)

The diphenylimidazole type dyes each represented by the Formula [I] or [II] may be synthesized by oxidation-coupling the couplers each represented by the following Formula [III] or [IV] to the paraphenylenediamine type developing agents each represented by the following Formula [V], in the presence of an axidizing agent:

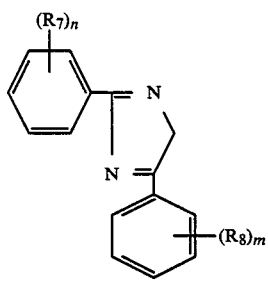   Formula [III]

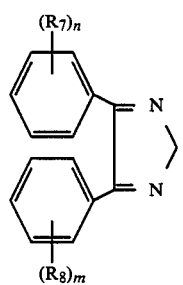   Formula [IV]

Wherein $R_7$, $R_8$, n and m are synonymous with those denoted in the aforegoing Formulas [I] and [II], respectively.

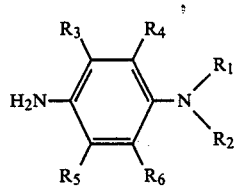   Formula [V]

Wherein $R_1$, $R_2$, $R_3$, $R_4$, $R_5$ and $R_6$ are synonymous with those represented by the Formulas [I] and [II].

It is preferred to progress the above-mentioned oxidation-coupling process under the basic conditions, and the reaction media may be any one of an organic solvent, aqueous organic solvent or the aqueous solutions thereof. As for the oxidizing agent, any of them may be used, provided that they have such an electric potential as is capable of oxidizing a p-phenylenediamine, regardless of the organic or inorganic type. Such oxidizing agents capable of being used include, for example, a variety of inorganic oxidizing agents such as a silver halide, hydrogen peroxide, manganese dioxide, potassium persulfate, oxygen atom and so forth and a variety of organic oxidizing agents such as N-bromosuccinimide, Chloramine T and so forth.

The cyan dyes of the invention may be prepared by oxidation-coupling diphenylimidazole type couplers to a p-phenylenediamine, as described above, and such diphenylimidazoles may be synthesized in such a process as described in, for example, Ber, 34, 639, Franz Kunchell; Ber, 38, 1536, A. Pinner; and so forth, or in such a literature as those of Ber, 29, 2103, Stephan S. Minovici; and so forth.

The typical synthesis examples will now be given below:

SYNTHESIS EXAMPLE 1 [SYNTHESIS OF COMPOUND EXAMPLE (2)]

Synthesis of 2,4-diphenylimidazole

A dissolution of 7 g of a benzamidine chloride was made in 30 ml of water. The resulted solution was further added with a solution of 5 g of caustic potash dissolved in 15 ml of water, so that benzamidine was deposited. The resulted matter was added with 20 ml of chloroform and the whole amount of the solution was poured into a separating funnel and was then shaken well so as to separate a chloroform layer.

The resulted chloroform solution was added with 3.0 g of bromoacetophenone while stirring and, next, the resulted solution was boiled and refluxed for 3 hours.

When the chloroform was vacuum-distilled off therefrom, an oily matter remained. When the oily matter was washed well several times in warm water, it was crystallized. Next, when it was recrystallized with 10 ml of alcohol, 2.0 g of a white powder were obtained. Melting point: 168° to 175° C.

SYNTHESIS OF DYE [COMPOUND EXAMPLE (2)]

A dissolution of 5 g of 2,4-diphenylimidazole was made in 3 liters of water, 100 g of potaasium carbonate and 2 liter of alcohol. Next, while stirring the resulted solution at room temperature, the solution of 11 g of 4-amino-3-methyl-N-ethyl-N-($\beta$-methanesulfonamidoethyl)anilinesulfonate dissolved in 200 ml of water was added thereto.

Then, the solution of 15.8 g of potassium persulfate dissolved in 300 ml of water was dropped into the resulted matter for 5 minutes. After the dropping was completed, the reaction was kept going as it was for 30 minutes at room temperature. Further, 3 liters of water was added thereto, so that the deposited crystals were filtrated. After the crystals were washed well and dried. Thereby, 13 g of the unrefined crystals were obtained. The resulted unrefined crystals were then refined in a silica gel chromatography.

As for the eluent, a mixed solvent of toluene and ethyl acetate at a proportion of 60:25 (by volume) was used. Further, the resulted dye crystals were recrystallized with toluene, so that 5 g of pure dyes were ontained. Melting point: 157° to 159° C.

SYNTHESIS EXAMPLE 2 [SYNTHESIS OF COMPOUND EXAMPLE (8)]

4,5-diphenylimidazole may be synthesized in accordance with the aforegoing literatures, however, they may be available from Aldlich Company.

SYNTHESIS OF DYES [COMPOUND EXAMPLE (8)]

The dyes were synthesized in the same manner as in the above-mentioned synthesis, except that 5 g of 4,5-diphenylimidazole was replaced by 2,4-diphenylimidazole and 14 g of the resulted unrefined crystals were recrystallized with 100 ml of acetonitrile. Resultingly, 7.7 g of pure dye crystals were obtained. Melting point: 146° to 151° C.

SYNTHESIS EXAMPLE 3 [SYNTHESIS OF COMPOUND EXAMPLE (3)]

Synthesis of 2-phenyl-4-(o-stearylamidophenyl)imidazole

A solution was prepared by dissolving 4.0 g of benzamidine sulfate in 20 ml of water, and the resulted solution was added with a solution of 3.3 g of caustic potash dissolved in 7.5 ml of water. Next, 15 ml of chloroform were added therein. The whole amount of the resulted solution was poured into a separating funnel and was then shaked well so as to extract free benzamidine in a chloroform layer. After the chloroform layer was separated therefrom, 3.0 g of o-stearylamidophenacyl bromide was added into the resulted matter. After the resulted solution was boiled and refluxed for 2 hours and was then cooled, the chloroform was distilled off under reduced pressure. The residues were washed several times with water and were then crystallized by adding 100 ml of methanol. The filtrated unrefined crystals were recrystallized with an ethyl acetate-methanol mixed solution. Melting point: 169° to 174° C.

SYNTHESIS OF DYES [COMPOUND EXAMPLE (3)]

A solution was prepared by dissolving 6.3 g of 2-phenyl-4-(o-stearylamidophenyl)imidazole in 500 ml of ethyl acetate. The resulted solution was added with a solution of 50 g of potassium carbonate dissolved in 500 ml of water and was then stirred at room temperature.

Next, the resulted solution was added with a solution of 5.5 g of 4-amino-3-methyl-N-ethyl-N-($\beta$-methansulfonamidoethyl)aniline surfate dissolved in 100 ml of water. Further, the resulted solution was added while stirring by dropping a solution of 8.75 g of potassium persulfate dissolved in 100 ml of water. After the resulted matter was stirred for 30 minutes as it was, the resulted aqueous layer was separated therefrom. After washing with 500 ml of water two times, the resulted ethyl acetate layer was dehydrated and was then condensed under reduced pressure. The resulted residue was treated in a silica gel chromatographic process. The proportion of the eluting solution was toluene:ethyl acetate=9:1.

Yield: 4.3 g.

Melting point: 126° to 130° C.

SYNTHESIS EXAMPLE 4 [SYNTHESIS OF COMPOUND EXAMPLE (14)]

This example was synthesized in the same manner as in Synthesis Example 3, except that the o-stearylamidophenacyl bromide used in Example 3 was replaced by o-($\alpha$-{2,4-di-t-amylphenoxy}hexanamido)phenacyl bromide.

Melting point: 148° to 150° C.

The diphenylimidazole dyes of the invention are particularly useful for the cyan dyes for photographic use capable of reproducing cyan images in such a manner either that a coupler represented by the aforegoing Formula [III] or [IV] is used as a cyan coupler for a silver halide color photographic light-sensitive material, for example, and the light-sensitive material is developed with a color developer containing a p-phenylenediamine type color developing agent represented by the aforegoing Formula [V] or that a silver halide photographic light-sensitive material not containing coupler is developed by a developer containing the coupler represented by Formula [III] or [IV] and a p-phenylenediamin type color developing agent represented by Formula [V], and, then, the coupler is coupled to the p-phenylenediamine type color developing agent which was oxidized by the exposed silver halide.

The diphenylimidazole dyes of the invention are also useful for the filter dyes for photographic use as well as for the cyan dyes for image reproduction use in a thermal transfer process, an ink-jet process, a color electrophotographic process, printing process and so forth, such as described in Japanese patent O.P.I. publication Nos. 149048/1983, 18169/1983, 205798/1983, 219086/1983 and so forth.

The dyes of the invention may be used together with any well-known stabilizers so as to improve the stability against light or heat. Such stabilizers include, for example, hydroquinone derivatives such as those described in U.S. Pat. Nos. 3,935,016 and 3,982,944; hydroquinone diether derivatives such as those described in U.S. Pat. No. 4,254,216 and Japanese patent O.P.I. publication No. 21004/1980; phenol derivatives such as those described in Japanese patent O.P.I. publication No. 145530/1979; spiroindan derivatives and methylenedioxybenzene derivatives, such as those described in British Pat. Nos. 2,077,455 and 2,062,888; chroman derivatives, spirochroman derivatives and coumarin derivatives, such as those described in U.S. Pat. Nos. 3,764,337, 3,432,300, 3,574,627 and 3,573,050, and Japanese patent O.P.I. publication Nos. 152225/1976, 20327/1978 and 17729/1978; hydroquinone monoether derivatives and p-aminophenol derivatives, such as those described in Japanese patent O.P.I. publication No. 6321/1980, British Pat. No. 1,347,556, British patent publication open to public inspection No. 2,066,975, and Japanese patent examined publication No. 12337/1979; bisphenol derivatives such as those described in Japanese patent examined publication No. 31625/1973 and U.S. Pat. No. 3,700,455; metal complexes such as those described in U.S. Pat. No. 4,245,018 and so forth; and the like stabilizers.

The cyan dyes of the invention are useful for the cyan dyes for forming color images in a color-subtraction process, and they are also useful for the filter dyes used in the form of a green- or blue-filter mixed together with a yellow or magenta dye. Such filters may be applied to, for example, a solid-state image-sensor tube, a liquid-crystal color television set and so forth.

At least in the above-mentioned application, the dyes of the invention are very excellent in hue to serve as cyan dyes, high in mol-absorption coefficient (E), and also high in fastness against light and heat.

In the dyes of the invention, as compared with the well-known phenol type or naphthol type indoaniline cyan dyes, the waveform on the short-wave side of the hue spectral transmittance curve is sharply dropped, so that the side absorption in the red region is sharply reduced and irregular absorption is relatively less and, further, the mol-absorption coefficient in the red spectral region is about three times as larger as in the well-known dyes. The dyes of the invention also display both excellent light- and heat-fastness and very favorable characteristics for color photographic use from the viewpoint of color reproduction.

In the dyes of the invention, as compared with the well-known dyes each formed through an oxidation-coupling reaction of a diphenylimidazole with an aminophenol, the pH dependence is more improved. Namely, when no quaternary mordant is present, a λ maximum is not shortened in absorption wavelength in a neutralized condition.

EXAMPLE

With respect to the above-mentioned exemplified compounds (2), (3), (8) and (14) of the dyes of the invention and the undermentioned comparative dyes (A) and (B), each of the absorption spectra and the mol-absorption coefficients (E) in the visible light region were measured in a ethyl acetate solution. The results thereof are shown in the table below.

TABLE

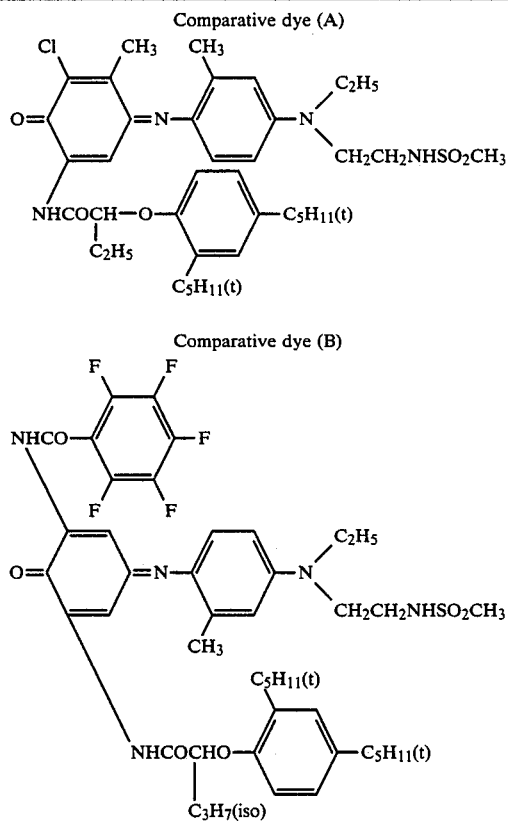

| Dye | λ max (nm) | Δλ (0.2) (nm) | ε | Δλ ½ (nm) |
|---|---|---|---|---|
| Exemplified (2) | 600 | 78 | 57,500 | 81 |
| Exemplified (3) | 642 | 79 | 69,900 | 84 |
| Exemplified (8) | 606 | 81 | 51,200 | 91 |
| Exemplified (14) | 637 | 80 | 68,800 | 83 |
| Comparative (A) | 644 | 100 | 23,400 | 118 |
| Comparative (B) | 636 | 108 | 18,200 | 123 |

[Note]
(1) Δλ (0.2) means a value of characteristic curve inclination on the short wavelength side of a spectral absorption, and is defined as a difference between a wavelength λ (0.2) on the short wavelength side of a spectral transmittance curve where an absorbance is to be 20% of the absorbance at a λ max and the λ max, and it is defined as, namely, Δλ (0.2) = λ max − λ (0.2)
(2) λ ½ = A half-band width As described above, it is found that the cyan dyes of the invention may be able to substantially display a sharp-cut absorption and a high mol-absorption coefficient (E), as compared with any conventional phenol type cyan dyes.

When using the dyes of the invention to serve as cyan dyes for forming images, the above-mentioned facts mean that a certain density can be obtained with a relatively less amount of dyes, and the sharp inclination of a spectral absorption characteristic curve means a less side-absorption in green spectral region. The facts also indicate that the dyes of the invention is excellently advantageous for color reproduction.

What is claimed is:

1. A diphenylimidazole type dye represented by the following Formula [I] or [II]:

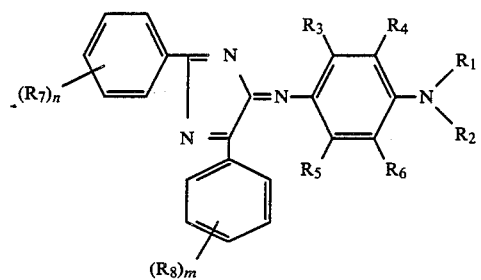

Formula [I]

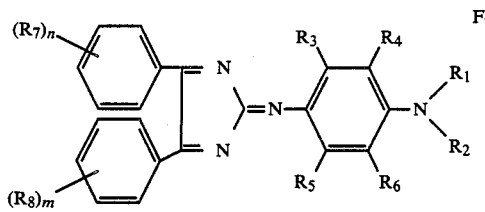

Formula [II]

wherein $R_1$ and $R_2$ represent each a hydrogen atom, an alkyl group or a substituted alkyl group, and $R_1$ and $R_2$ may be coupled to each other so as to complete a 5- or 6-membered ring optionally containing a hereto atom; $R_3$, $R_4$, $R_5$ and $R_6$ represent each a halogen atom, an alkyl group, a substituted alkyl group, an alkoxy group or a substituted alkoxy group; $R_7$ and $R_8$ represent each a halogen atom, or a monovalent substituent; n and m are each an integer of from 0 to 5, provided that, when n is an integer of not less than 2, $R_7$s may be the same with or different from each other and that, when m is an integer of not less than 2, $R_8$s may be the same or different from each other.

2. The diphenylimidazole type dye of claim 1, wherein $R_1$ or $R_2$ each represent a hydrogen atom, an alkyl group, a hydroxyalkyl, an alkoxyalkyl group, an alkoxyalkoxyalkyl group or an alkylsulfonamidoalkyl group.

3. The diphenylimidazole type dye of claim 1, wherein said 5-or 6-membered completed by coupling of $R_1$ and $R_2$ is a pyrrolidino group, a piperidino group, a piperazino group or a morpholino group.

4. The diphenylimidazole type dye of claim 1, wherein $R_3$, $R_4$, $R_5$ and $R_6$ each represent a hydrogen atom, a halogen atom, an alkyl group, a hydroxyalkyl group, an alkoxy alkyl group, an alkylsulfonamidoalkyl group or an alkoxy group.

5. The diphenylimidazole type dye of claim 1, wherein $R_7$ or $R_8$ represent each a halogen atom, a nitro group, a hydroxy group, an amino group, an alkyl group, an alkoxy group, an alkylamido group, an arylamido group, an alkylsulfonamido group, an arylsulfonamido group, a dialkylcarbamoylamino group, a dialkylsulfamoylamino group, an alkoxycarbonylamino group, an aryloxycarbonylamino group and an arylcarbamoylamino group.

6. The diphenylimidazole type dye of claim 5, wherein said group represented by $R_7$ or $R_8$ is coupled at least one of ortho positions of the phenyl groups with respect to the position to which an imidazole ring is coupled, and said $R_7$ or $R_8$ is a hydroxyl group, an amino group, an alkylamido group, an arylamido group, an alkylsulfonamido group, an arylsulfonamido group, a dialkylcarbamoylamino group, a dialkylsulfamoylamino group, an alkoxycarbonylamino group, an aryloxycarbonylamino group or an arylcarbamoylamino group.

7. The diphenylimidazole type dye of claim 6, wherein said group coupled in the ortho position of the phenyl group is an alkylamido group, an arylamido group, an alkylsulfonamido group, or arylsulfonamido group.

* * * * *